(12) United States Patent
Schmocker et al.

(10) Patent No.: US 10,945,739 B2
(45) Date of Patent: Mar. 16, 2021

(54) DEVICE AND METHOD FOR INJECTION, PHOTOACTIVATION AND SOLIDIFACTION OF LIQUID EMBOLIC MATERIAL IN THE VASCULAR SYSTEM OR OTHER ORGANIC CAVITIES

(71) Applicant: ECOLE POLYTECHNIQUE FEDERALE DE LAUSANNE (EPFL), Lausanne (CH)

(72) Inventors: Andreas Schmocker, Lausanne (CH); Christophe Moser, Lausanne (CH); Pascal Mosimann, Lausanne (CH)

(73) Assignee: Ecole Polytechnique Federale de Lausanne (EPEL), Lausanne (CH)

( * ) Notice: Subject to any disclaimer, the term of this patent is extended or adjusted under 35 U.S.C. 154(b) by 6 days.

(21) Appl. No.: 15/574,439

(22) PCT Filed: May 20, 2016

(86) PCT No.: PCT/IB2016/052977
§ 371 (c)(1),
(2) Date: Nov. 15, 2017

(87) PCT Pub. No.: WO2016/185440
PCT Pub. Date: Nov. 24, 2016

(65) Prior Publication Data
US 2018/0140303 A1 May 24, 2018

(51) Int. Cl.
*A61B 17/12* (2006.01)
(52) U.S. Cl.
CPC .. *A61B 17/12113* (2013.01); *A61B 17/12027* (2013.01); *A61B 17/12195* (2013.01); *A61B 2017/1205* (2013.01)

(58) Field of Classification Search
CPC ........ A61B 17/12027; A61B 17/12113; A61B 17/12195; A61B 2017/1205
See application file for complete search history.

(56) References Cited

U.S. PATENT DOCUMENTS

| 5,108,407 A | 4/1992 | Geremia et al. |
| 5,443,454 A | 8/1995 | Tanabe et al. |
| (Continued) | | |

FOREIGN PATENT DOCUMENTS

| DE | 4028466 | 3/1992 |
| EP | 0664104 | 7/1995 |
| (Continued) | | |

OTHER PUBLICATIONS

International Search Report and Written Opinion prepared by the European Patent Office dated Sep. 20, 2016, for International Application No. PCT/IB2016/052977.

*Primary Examiner* — Jocelin C Tanner
(74) *Attorney, Agent, or Firm* — Muncy, Geissler, Olds & Lowe, P.C.

(57) ABSTRACT

The present invention concerns an organic cavity injection device including an injection cannula for injecting a photo-activatable substance inside an organic cavity; at least one element or a plurality of elements configured to control the removal of a resident substance from the organic cavity and simultaneously prevent removal of the non-activated photo-activatable substance from the organic cavity; and an optical waveguide for providing electromagnetic radiation inside the organic cavity to the photo-activatable substance to photoactive the photo-activatable substance inside the organic cavity.

23 Claims, 9 Drawing Sheets

(56) References Cited

U.S. PATENT DOCUMENTS

| | | | |
|---|---|---|---|
| 5,662,712 A | 9/1997 | Pathak et al. | |
| 5,709,653 A * | 1/1998 | Leone | A61M 25/1027 |
| | | | 604/103.01 |
| 5,725,568 A | 3/1998 | Hastings | |
| 5,749,894 A | 5/1998 | Engelson | |
| 5,860,948 A * | 1/1999 | Buscemi | A61B 17/0057 |
| | | | 604/20 |
| 6,096,021 A * | 8/2000 | Helm | A61B 17/12113 |
| | | | 604/103.01 |
| 6,299,597 B1 * | 10/2001 | Buscemi | A61F 2/82 |
| | | | 604/101.03 |
| 6,551,303 B1 | 4/2003 | Van Tassel et al. | |
| 8,814,826 B2 * | 8/2014 | Foreman | A61M 25/1011 |
| | | | 604/96.01 |
| 2002/0128697 A1 * | 9/2002 | Carrison | A61N 5/0601 |
| | | | 607/92 |
| 2002/0165572 A1 * | 11/2002 | Saadat | A61B 17/12022 |
| | | | 606/194 |
| 2002/0165582 A1 * | 11/2002 | Porter | A61B 17/12195 |
| | | | 606/213 |
| 2002/0165593 A1 * | 11/2002 | Hayashi | A61N 1/40 |
| | | | 607/88 |
| 2006/0184246 A1 | 8/2006 | Zwirkoski | |
| 2007/0255287 A1 | 11/2007 | Rabiner | |
| 2008/0004686 A1 * | 1/2008 | Hunt | A61F 2/2418 |
| | | | 623/1.11 |
| 2008/0033341 A1 * | 2/2008 | Grad | A61B 18/24 |
| | | | 604/20 |
| 2008/0033523 A1 * | 2/2008 | Gale | A61F 2/958 |
| | | | 623/1.11 |
| 2008/0039854 A1 | 2/2008 | Rabiner | |
| 2008/0154234 A1 | 6/2008 | Behravesh et al. | |
| 2010/0063493 A1 * | 3/2010 | Anastasie | A61B 18/24 |
| | | | 606/15 |
| 2010/0099946 A1 * | 4/2010 | Jenkins | A61B 1/126 |
| | | | 600/104 |
| 2010/0119605 A1 | 5/2010 | Isenburg et al. | |
| 2011/0313356 A1 | 12/2011 | Rabiner et al. | |
| 2015/0157405 A1 * | 6/2015 | Beeckler | A61B 18/20 |
| | | | 606/13 |

FOREIGN PATENT DOCUMENTS

| | | |
|---|---|---|
| EP | 1688097 | 8/2006 |
| EP | 2676696 | 12/2013 |
| GB | 2493100 | 1/2013 |
| JP | 2008-253516 | 10/2008 |
| KR | 2014-0057158 | 5/2014 |
| WO | WO 95/08289 | 3/1995 |
| WO | WO 99/02093 | 1/1999 |
| WO | WO 00/72781 | 12/2000 |
| WO | WO 02/45596 | 6/2002 |
| WO | WO 02/087449 | 11/2002 |
| WO | WO 2004/045393 | 6/2004 |
| WO | WO 2006/062916 | 6/2006 |
| WO | WO 2006/108114 | 10/2006 |
| WO | WO 2007/113833 | 10/2007 |
| WO | WO 2007/127260 | 11/2007 |
| WO | WO 2009/036576 | 3/2009 |

* cited by examiner

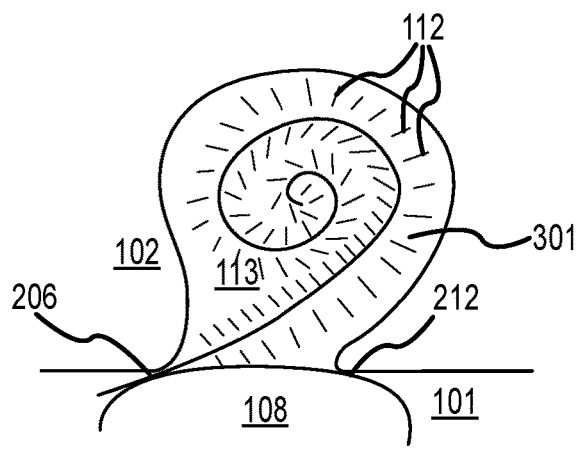
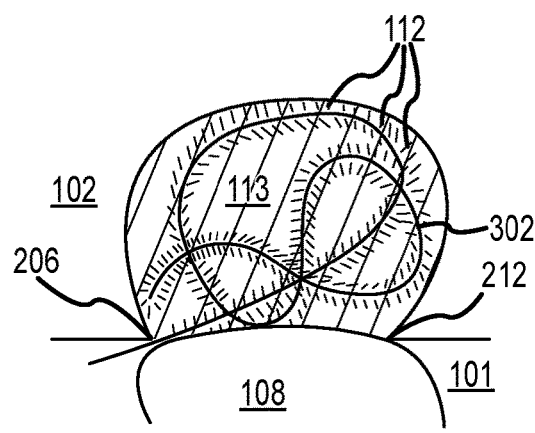
FIG.7a        FIG.7b
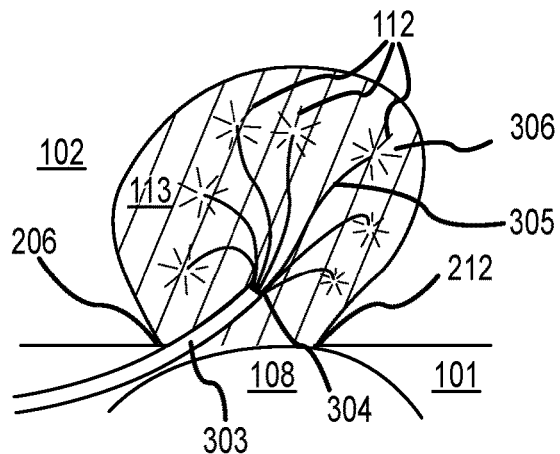
FIG.8
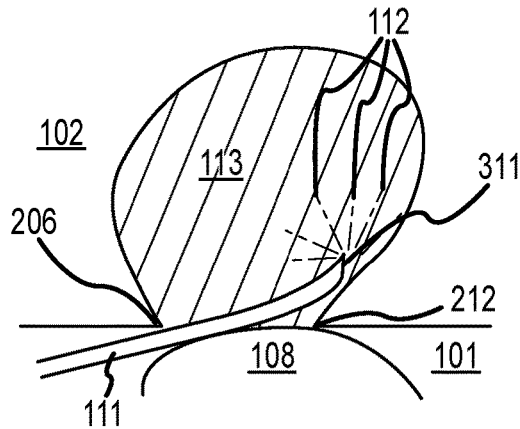
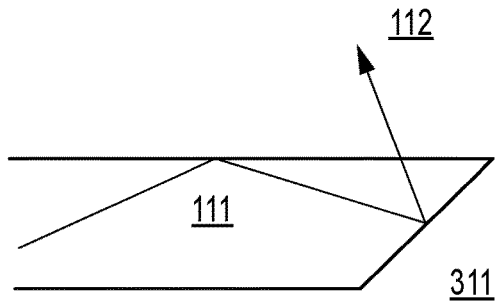
FIG.9a        FIG.9b

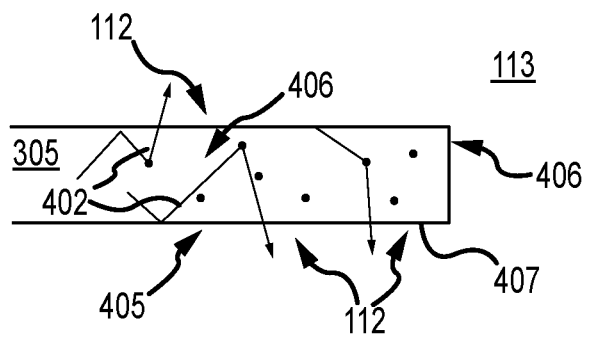 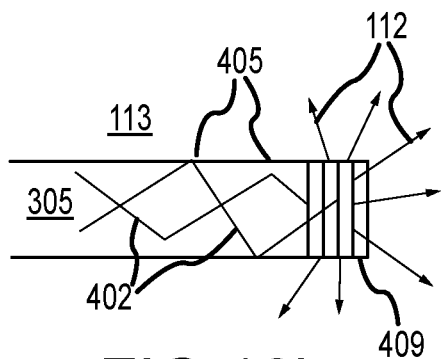
FIG.18a  FIG.18b
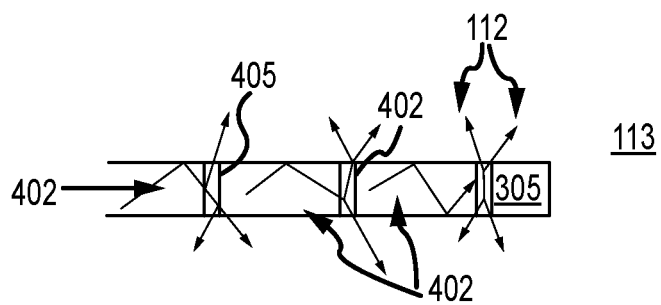
FIG.18c
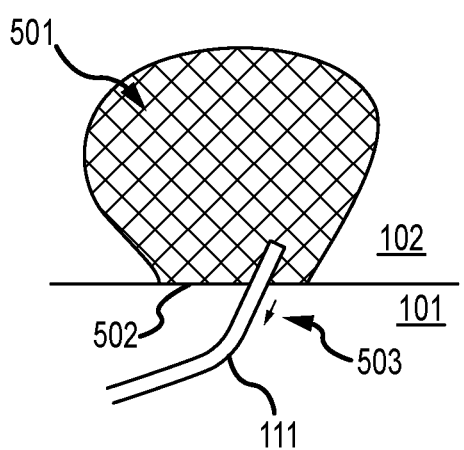 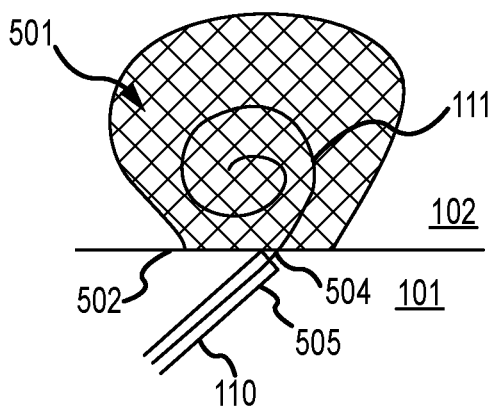
FIG.19a  FIG.19b

DEVICE AND METHOD FOR INJECTION, PHOTOACTIVATION AND SOLIDIFACTION OF LIQUID EMBOLIC MATERIAL IN THE VASCULAR SYSTEM OR OTHER ORGANIC CAVITIES

CROSS REFERENCE TO RELATED APPLICATIONS

This application is a national stage application under 35 U.S.C. 371 and claims the benefit of PCT Application No. PCT/IB2016/052977 having an international filing date of 20 May 2016, which designated the United States, which PCT application claimed the benefit of International Bureau of the World Intellectual Property Organization Application No. PCT/IB2015/053738 filed 21 May 2015, the disclosure of each of which are incorporated herein by reference.

FIELD OF THE INVENTION

The present invention generally relates to photopolymerization devices and more particularly to devices that uses light to harden, activate, control or change the chemical and physical state of a photo-chemically active or responsive material, as well as the delivery methods thereof into a living subject. The invention relates more specifically to a photo-activating device and a photo-sensitive liquid agent to treat or cure vascular or cardiac anomalies such as arterial aneurysms of the brain, aorta or other locations, as well as certain cardiac defects. The treatment combination also involves a light-controlled polymerization reaction to solidify the injected liquid agent in the targeted cavity with light transmitted through a laser-controlled detachable light-conducting system. The device for controlled injection, illumination and polymerization reaction may be inserted through a catheter system used for endovascular surgery. A broader range of applications of the same concept to other bodily cavities amenable to endovascular procedures such as venous, dental, cosmetic or orthopedic anomalies for instance, is also part of the invention.

DISCUSSION OF THE BACKGROUND ART

The human cardio-vascular system may be subjected to several pathological conditions, such as an aneurysm, which is an abnormal focal dilatation or out-pouching of an artery. Aneurysms have a thinner and weaker wall than their parent artery and thus may rupture and bleed, often leading to death or severe neurological handicaps. Abdominal aortic aneurysms (AAA) and cerebral aneurysms are the most prevalent locations but these are also found in other areas such as, but not limited to, the renal arteries or the lower limbs, for instance.

Historically, intracranial aneurysms were treated with open head surgery (craniotomy) by placing a metallic or titanium clip around the neck of the aneurysm under a microscope to seal it off and prevent blood from entering and leaking out of the pouch. Although this technique still applies today, many aneurysms are challenging to handle surgically because of their location or configuration or because of the poor clinical condition of the patient.

Endovascular techniques have progressively emerged as the treatment method of choice for most aneurysms currently treated. These minimally invasive techniques allow one to cure an aneurysm by first navigating a catheter through the vascular system after having punctured, for instance the femoral artery to then occlude the aneurysm from within, thereby avoiding craniotomy and reducing short and long-term morbidity and mortality compared to craniotomy and clipping. Endovascular solid implants, also referred to as embolic (occlusive) agents, most commonly consist of platinum, or also stainless steel or tungsten coils—pre-shaped helical soft filaments—pushed through the microcatheter to the target site in order to fill the pouch. Coils are implanted to promote flow stagnation and thrombosis (clotting) of the aneurysm, thereby isolating the sac from the arterial circulation and eliminating or reducing the risk of blood leakage, i.e. intracranial bleeding. The embolic implants are engaged and delivered through the distal tip of the microcatheter by manually pushing proximally on a metallic micro-rod (pusher wire) that is attached to the coil. The coil can thus be retrieved and placed as desired by pushing or pulling on the pusher wire. Once the coil is considered to be adequately placed, precise release and controlled detachment from the pusher wire is achieved by the treating physician. Detachment is triggered by an electrolytic or mechanical reaction at the junction between the coil and the pusher wire induced by an electrode-containing docking station connected to the proximal end of the pusher wire. The pusher wire is then retrieved and discarded followed by the insertion and manipulation of another coil and so forth until the cavity is packed as densely as possible. Once the last coil has been placed, the microcatheter is carefully removed while avoiding displacing or fishing out one or more coils from the aneurysm into the parent artery. The whole endovascular procedure and delivery process is visualized by x-ray fluoroscopy. All materials and implants therefore require radio-opaque markers for precision and safety purposes.

Coil technology has evolved towards more complex implants including 3D shaped coils for wide-necked and irregular shaped aneurysms to better fill the aneurysm and avoid coil prolapse into the parent artery, as well as hydrogel coated coils that expand in contact with blood to enable a higher coil packing density.

Similarly, other solid embolic intra-sacular materials have been developed and are currently being assessed in human clinical trials, such as metallic cage-like implants called the WEB or LUNA devices (manufactured by Sequent Medical and Medtronic-Covidien-Ev3, respectively) designed to promote aneurysm thrombosis and intra-sacular flow disruption. In the early days of endovascular aneurysm treatment, detachable silicone balloons were used to occlude the sac but were rapidly abandoned because of their tendency to deflate and potentially migrate over time thereby failing to produce stable mid or long-term aneurysm occlusion.

Extra-sacular devices implanted in the parent artery such as nitinol and chromium-cobalt stents have also been developed to promote thrombosis of an aneurysm. Stents are often used in conjunction with coils to enhance flow stagnation inside the aneurysm, a technique called stent-assisted coiling. Stents are especially useful for wide-necked aneurysm where coils may not hold in the sac and migrate into the parent artery. Newer generation braided stents with a higher mesh density, also known as flow diverting stents (or simply flow diverters), were designed to be used alone without coils or other intra-sacular implants by redirecting blood flow in the parent artery and away from the aneurysm to reduce sacular inflow and induce shrinkage or disappearance of the aneurysm through thrombosis over the course of several months, a phenomenon coined "vessel remodeling".

Despite the many advantages of solid embolic agents, these are associated with several limitations and drawbacks. Intra-sacular implants such as coils or cage-like structures have to be sized correctly to fit the aneurysm in order to occlude it. Undersizing may lead to incomplete occlusion, while oversizing may traumatize the walls of the aneurysm and cause a rupture or prolapse of the material in the parent artery. Moreover, even correctly sized implants may fail to fully occlude an aneurysm that has a more complex shape than the implant, which is more often the rule than the exception.

Another major challenge with endovascular occlusion compared with surgical clipping is the risk of aneurysm recurrence, also referred to as recanalization. Because the current intra or extra sacular implants never occupy the whole volume of the aneurysm and work by inducing or promoting clotting inside the sac, there is a risk that the clot may change and dissolve over time and that solid implants such as coils may compact on themselves, causing the aneurysm to grow thereby potentially exposing the patient once again to a rupture. Aneurysm regrowth is much more likely to occur if the aneurysm is large (10 mm or more in diameter), has a wide neck (>4 mm), initially presented with a rupture or if it was incompletely occluded. Additionally, incompletely embolized aneurysms may be more difficult to subsequently clip, since the neck may be less accessible.

Another drawback associated with stents or other extra-sacular implants is the need for anti-platelet therapy. While such medication is necessary to avoid foreign body clotting reactions and reduce the risk of parent artery thrombosis—which can lead to severe brain infarction, neurological deterioration and death—antiplatelets can also lead to life-threatening conditions in case of bleeding.

Because each aneurysm is unique in shape and size, there is a strong need for an intra-sacular implant capable of filling the whole aneurysm volume, regardless of its morphology. One solution is the use of liquid embolic agents to occupy the whole sacular space.

Onyx-HD500 (manufactured by Medtronic-Covidien-Ev3) is a non-adhesive liquid embolic agent used for the embolization of brain aneurysms. Onyx HD500 is comprised of 20% EVOH (ethylene vinyl alcohol) copolymer dissolved in DMSO (dimethyl sulfoxide) and suspended micronized tantalum powder to provide contrast for visualization under fluoroscopy. Onyx HD500 (20% EVOH) is a device for the treatment of intracranial, saccular, sidewall aneurysms that present with a wide neck (≥4 mm) or with a dome-to-neck ratio <2 that are not amenable to treatment with surgical clipping. Once the liquid embolic composition is injected into the aneurysm, the DMSO solvent dissipates as it comes into contact with the ionic contents of the blood stream, causing the polymer to progressively solidify by means of precipitation. Virtually the same agent called SQUID (manufactured by Balt extrusion, Montmorency, France) also functions in the same way. A similar non-adhesive liquid embolic agent called PHIL (Precipitating Hydrophobic Injectable Liquid, manufactured by Microvention) is also available on the market. Like Onyx and SQUID, PHIL precipitates and solidifies as it comes into contact with the ionic content of the blood stream and DMSO progressively dissipates. The radio-opaque material for visualization under fluoroscopy is iodine (instead of tentalum powder for Onyx). Other liquid embolic agents made of acrylic glue that solidifies by means of polymerization in contact with blood instead of precipitation also exist. Solidification is much more rapid and almost impossible to stop once injected. The two most common polymerazing agents are Histoacryl (B. Braun, Germany) and Glubran (GEM, Italy) which solidify by polymerization. Radio-opacity of both polymerizing agents is achieved by mixing the glue with lipiodol (labeled Ethiodol in the USA), also known as ethiodized oil, made from poppyseed oil containing iodine. Glubran-2 is a synthetic surgical glue, CE certificated, for internal and external use, with haemostatic, adhesive, sealer and bacteriostatic properties. When used in a moist environment, it quickly polymerizes into a thin elastic film that has high tensile strength and firmly adheres to the anatomy of the tissue on which it is applied. Once polymerized, Glubran-2 acts as a bioinert material that is used in open and laparoscopic surgery, as well as in endovascular surgery as an embolic agent. Histoacryl consists of monomeric n-butyl-2-cyanoacrylate, which polymerises quickly in contact with tissue fluid.

Despite their capacity to fill a complex shape or volume more completely than solid implants, liquid embolic agents have their own limitations.

Depending on the rate at which a precipitating liquid embolic agent (Onyx, Squid, PHIL) is injected into the blood vessel and depending on the speed of blood flow, the polymer may remain in liquid form for a period of time while the solvent dissipates into the blood stream, causing small strings of unsolidified polymer material to separate from the polymer mass. This may lead to the embolic agent getting washed out of the aneurysm and migrate back to the parent artery and flushed downstream where it may solidify and occlude other structures unintentionally, causing ischemic stroke.

Likewise, polymerization agents such as Histoacryl or Glubran may get washed out and solidify in the parent artery or downstream depending on their dilution/concentration mix with lipiodol, their rate of injection and the intrinsic speed of blood flow, making the process of selective embolization of the aneurysm only with polymerizing agents almost impossible to control. Moreover, solidification through polymeriztion is almost instantaneous and highly thrombogenic, which may cause an irreversible extension of thrombosis from the aneurysm to the parent artery.

Although solidification is more controllable with precipitating agents like Onyx, Squid or PHIL, these materials tend to harden in a centripetal fashion through concentric layering similar to onion skins, hardening progressively from outside-in. Inflating a balloon inside the parent artery to prevent the agent from leaking out of the neck of the aneurysm is advised but does not fully prevent leakage of the agent and also exposes the artery to a possible rupture by the balloon inflation. Moreover, the vasotoxicity of DMSO contained in the agent has been reported to induce delayed rupture of the aneurysm wall and is currently rarely performed in routine practice. Additionally, one may have trouble to evaluate the full occlusion of the aneurysm since the first outer layer of hardened material will mask the inner content and prevent the operator from visualizing the subsequent material layerings.

Accordingly, it would be desirable to provide a device and delivery method to selectively control the solidification process of a biocompatible liquid polymer material inside an aneurysm while avoiding unintended spillage of the solidified material into the parent artery and blood stream. Ideally the injected unsolidified liquid polymer material would be inert, easily metabolized and would not solidify in contact with blood so that it could be safely injected in the blood stream without causing a toxic reaction or premature vessel occlusion. It would also be desirable to have a system where the interface between the parent artery and the aneurysm neck could be controlled actively and precisely with an on-off controllable triggering effect to avoid spillage of hardened material in the parent artery.

SUMMARY

One aspect of the present invention thus concerns an injection device according to claim 1. Another aspect of the present invention relates to an injection method according to claim 10.

Other advantageous features can be found in the dependent claims.

In light of the above problems and challenges, a solution to the described issues according to an aspect of the present invention is to inject an entire photo-sensitive implant (or a part of it) in liquid or semi-liquid form and then harden the material in situ by a photo chemical reaction. Photo-active materials such as photopolymers, once injected, can be illuminated with light in the visible or ultraviolet spectrum. The absorbed photons change the energy levels of electrons which then trigger the chemical reaction by creating free radicals, cations or anions which will induce the activation such as a solidification of the polymer in a controlled manner, similar to growing snowflakes at every point where the photons impinge onto the material. To place such materials in a minimally invasive way it is preferable to access the aneurysm with an injection device such as a catheter and a light delivery system such as an optical fiber connected to a light source to ensure the selective illumination of the injected material.

An element such as a balloon may be inflated in the parent artery in front of the neck of the aneurysm to better control the wash-in and wash-out of the injected photo-sensitive liquid agent. The balloon can be inflated with a solution that would either prevent light transmission (absorption) or enhance light refraction (mirror) to avoid inducing the hardening reaction outside of the aneurysm.

The present invention relates to a device structure and physical apparatus to inject and place a photosensitive material, and photopolymerize or activate the latter material using actinic light, and place a structural material within and/or around the photosensitive material.

In a preferred aspect, the photocurable material is a material that, once photocured, transforms from a fluid pre-polymeric condition to a polymeric, non-fluent condition.

It is among the general objects of the invention to also provide for techniques to effectively and efficiently applying a fluent polymerizable material to a target site, including living hosts' tissues, and for effecting polymerization of the fluent light-sensitive material in situ in an optimal way so as to obtain a desired degree of polymerization conferring to the applied material the best possible physical and/or chemical properties.

In a further aspect, the invention thus provides for a method of applying a material into or onto a tissue or cavity, the method comprising applying from an applicator an initially entirely fluent, pre-polymeric photocurable material to the tissue or cavity, applying actinic light through at least one light-transmitting element to the photocurable material from a light source that emits actinic light for a period of time sufficient to convert the entirely fluent, pre-polymeric photocurable material to a polymeric, non-fluent material, the polymeric, non-fluent material being in an amount effective to cover at least a portion of the target tissue, wherein the applicator is a tubular element comprising said at least one light-transmitting element and at least one interspace between said at least one light-transmitting element and the whole-length internal side of the wall of the tubular element, and wherein the initially entirely fluent, pre-polymeric photocurable material is applied into or onto the tissue or cavity through release from the distal end of said applicator.

The above and other objects, features and advantages of the present invention and the manner of realizing them will become more apparent, and the invention itself will better be understood from a study of the following description with reference to the attached drawings showing some preferred embodiments of the invention.

BRIEF DESCRIPTION OF THE FIGURES

The above object, features and other advantages of the present invention will be best understood from the following detailed description in conjunction with the accompanying drawings, in which:

FIGS. 7(*a*) and (*b*) depict snail like illumination options;

FIG. 8 depicts a tree-like illumination option;

FIGS. 9(*a*) and (*b*) depict another illumination option;

FIG. 18 shows further details of primary or secondary fibers or their tips;

FIGS. 19(*a*) and (*b*) illustrate detachment options for fibers;

DETAILED DESCRIPTION OF THE INVENTION

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

Figure 1A:
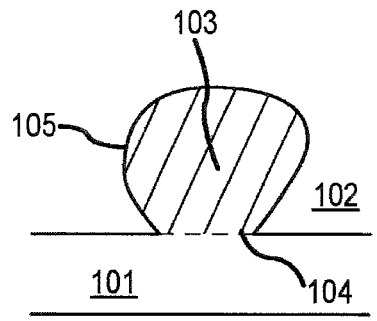
FIGS. 1(*a*) and (*b*) are views of a completely occluded (i.e. cured) aneurysm, the sac has been excluded from the arterial circulation—i.e. no more blood flowing into the aneurysm.
Figure 1B:
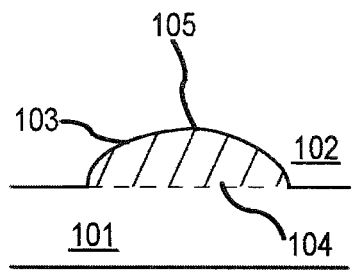

FIGS. 1(a) and (b) show examples of repaired cavities, such as an aneurysm. A vessel 101, for example a blood vessel, expands into a cavity or sack delimited by the boundary 105 and surrounded by tissue 102. The space within the cavity 103 needs to be filled up with a material. This can be an implanted filler or also a material or structure placed to induce a reaction such as an embolism. The goal is to form a boundary 104 between the vessel and the cavity. The cavity can be of any shape. It can have one or several entries to access it.

Figure 2A:
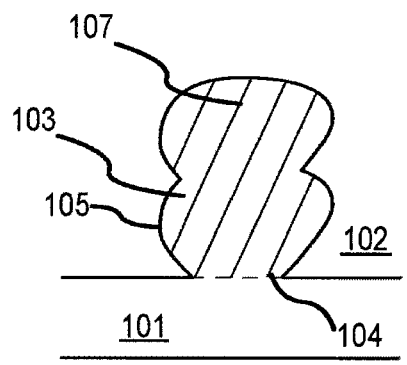
FIGS. 2(*a*) and (*b*) show how an aneurysm previously treated by other means (coil mass or intrasaccular flow disruption device) can be further embolized with a liquid photosensitive material to achieve cure.
Figure 2B:
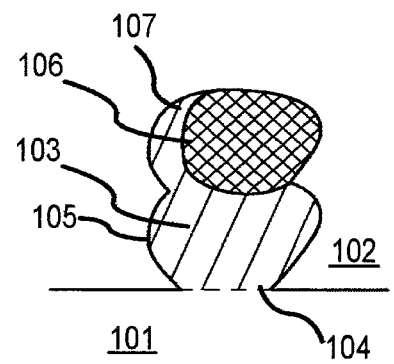

FIGS. 2(a) and (b) illustrate other cavity options. In this case the cavity consists of two sacks to be filled, a lower 103 and upper one 107. Furthermore it is possible that within a cavity or within a part of a cavity other objects (106) are placed previously. In such a case the space to be filled might surround these objects or, if these objects are hollow, be inside the objects.

Figure 3:
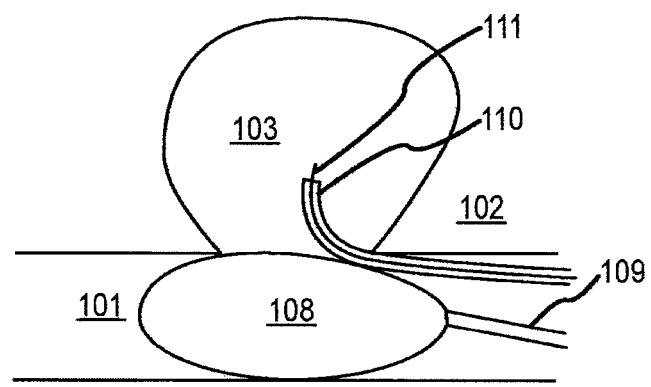
FIG. 3 illustrates a device according to an aspect of the present invention.

FIG. 3 is a global view of one aspect of the present invention. First an object 108, such as for example an inflatable balloon, is placed in front of the cavity or in front of the cavity entries. This object is placed by using an applicator 109, for instance a cannula through which a balloon is guided and then inflated to reach a desired shape. One important feature of the invention is a second cannula 110. This cannula can be flexible or stiff. It is placed before placing the object 108, or the object 108 is used to guide the cannula 110 into the cavity. Another function of the object 108 can be to interrupt the flow in the vessel 101 and also in the cavity 103. Also other methods to place the cannula are imaginable such as the use of a guide wire which is placed first within the cavity. Another important feature is an optical light guiding element 111. This optical light guide can be brought into the cavity 103 using the cannula 110. It can also be placed before placing the cannula 110 using a third cannula, not shown in this figure, but similar to the cannula 110.

Figure 4:
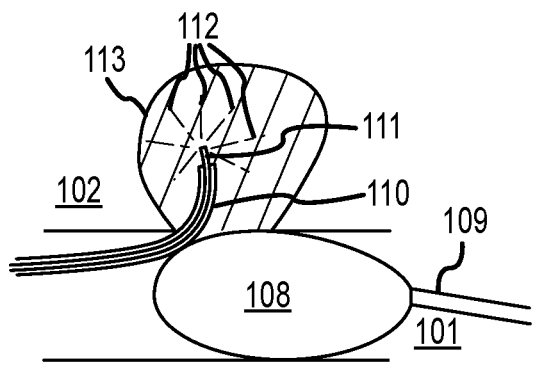
FIG. 4 depicts the concept of illumination and hardening of an injected material.

FIG. 4 shows another important feature of the invention that is the injection of a liquid photoactive material (LPM) 113 which is injected using the cannula 110. The light guiding element 111 illuminates the liquid material 113. Light 112 reaches the material. By illuminating the material it is activated. Such activation can for example consist of a photopolymerization, drug release or other.

A first aspect of the present invention thus relates to an organic cavity injection device or system including an injection cannula for injecting, for example, an LPM inside an organic cavity, an element configured to control the removal of a resident substance from the organic cavity and simultaneously prevent removal of the non-activated photo-activatable substance from the organic cavity, and an optical waveguide for providing electromagnetic radiation inside the organic cavity to the photo-activatable substance to photoactive the photo-activatable substance inside the organic cavity.

The element configured to control the removal of a resident substance from the organic cavity and simultaneously prevent removal of the non-activated photo-activatable substance from the organic cavity may be a balloon, a stent, a flow diverter, a deployed mesh-like three-dimensional structure, an element increasing or decreasing the hydrostatic pressure in the aneurysm, or an element inducing fluid suction or propulsion. Several of the above elements may be used together.

In one aspect, the invention provides for an illumination and injection device and/or implant, wherein said device is designed to interact with a photosensitive and/or a photo-curable material.

The device can comprise a light source. The light source emits actinic light. The device may further include an applicator having a proximal end and one or several distal ends and an elongated and/or bifurcated shaft therebetween and containing at least one light-transmitting element adapted to bidirectionally transmit light between said proximal end and said distal ends, wherein said proximal end of the applicator is operably connected to the light source.

The distal ends of the applicator can be arranged to emit actinic light originated from the light source to the photo-curable material and to capture light reflected or emitted by the photocurable material. Said implant can consist of the photosensitive and/or photocurable material, reinforcement materials and/or a parts of device. These parts of the device are between the distal end/s and the proximal end of the device and can be detached at a specific point by a detaching mechanism. This detaching mechanism can be a mechanical stress induced by a thermal energy, electromagnetic wave and/or externally applied mechanical energy and leads to a physical separation of the device. A light-guiding element which directs light travelling from the distal end of the applicator through the at least one light-transmitting element towards an optical detector can also be included the optical detector being capable of detecting the light reflected or emitted by the photocurable material.

The apparatus according to the present disclosure may comprise an optical system having one or several light sources, light-transmitting elements such as optical wave guides, light-guiding elements such as mirrors and/or beam combiners, free space and/or other optical subsystems to guide the light to the material to be illuminated.

In a preferred aspect, the light-transmitting elements of the illumination are optical fibers.

The light applied to and collected from the photosensitive material travels through an applicator having an elongated structure which allows photoactivation of materials on surfaces, in cavities, hollow recipients, tissues and within living organisms. In certain embodiments, the applicator is a cannula or a catheter containing optical fibers, connected to a light source. Optimal exposure of the photosensitive material to actinic light can be achieved by guiding the light close to the photosensitive material, for example to obtain an optimal degree of polymerization and thus the best possible physical properties of a photopolymerized material for a specific purpose.

Another aspect of the invention lies in the combination of the illuminating system with an injection system, allowing deposition of photosensitive material, illumination through one single applicator. In addition to one or more light transmitting elements, such an applicator contains at least one channel through which a fluid photocurable or otherwise photosensitive material can be injected or deposited at a target site such as a cavity or a living organism's tissue. Therefore, in a further aspect, the invention provides for an illumination device as disclosed above, wherein the applicator is a tubular element having a lumen and comprising at least one light-transmitting element placed within the lumen of the tubular element, and at least one interspace between said light-transmitting element and the internal side of the wall of said tubular element, and wherein said at least one interspace permits the delivery of a photocurable fluid material through the distal end of the applicator into or onto a cavity or a tissue of a living host.

In a particular aspect, the device of the invention further comprises a subsystem to introduce one or more fluids to the interspace between the light-transmitting element and the wall of the tubular element at or close to the applicator's proximal end, said fluids once mixed constituting a photocurable fluid destined to be applied into or onto a cavity or a tissue of a living host. In addition, the photocurable material can be put and possibly held under pressure in order to increase adherence to the surrounding tissue or cavity wall.

In a preferred aspect, the applicator is a cannula, a catheter or an endoscopic arm.

In a preferred aspect, the light guiding element has a diameter bellow 1 mm, ideally bellow 250 μm and even more ideally bellow 125 μm. In one aspect the intensity and illumination time of the light is adapted to affect (e.g. photocure) only injected material at a certain distance of the distal end. Thus, creating a controlled illuminated volume where injected material which is situated outside of this volume is not affected and can be, for instance, leave the body through the cardiovascular system. In addition such a volume can be further controlled during a surgery, by injecting and illuminating material in several steps and/or moving the optical light guide.

Figure 5A:
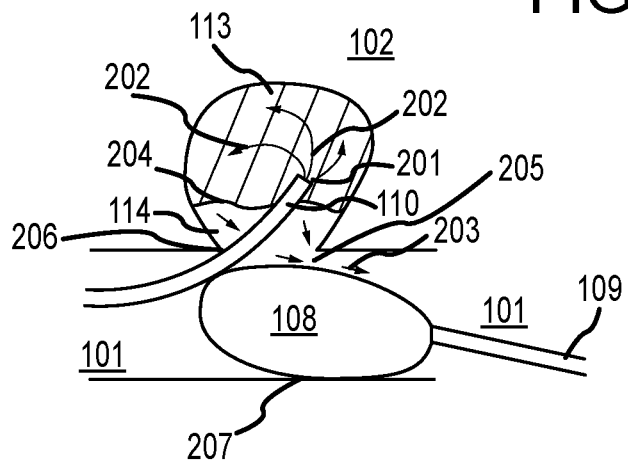
FIGS. 5(*a*) and (*b*) show injection methods based on forced flow and gravity.
Figure 5B:
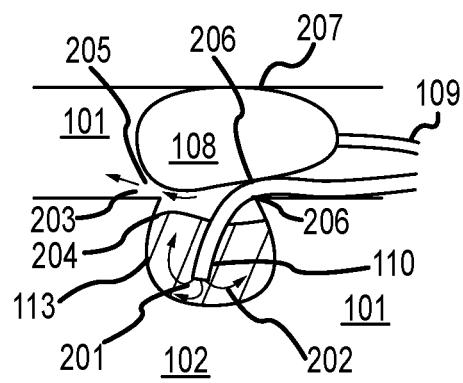

FIGS. 5(a) and (b) show another feature of the proposed device and method that is the placement of the LPM 113. In one embodiment the cannula 110 is placed inside the cavity at a position 201 between the middle of the cavity and the wall opposite of the entry. The injected liquid material 103 flows out or is ejected out of the cannula 110. This flow 202 starts to fill the inner part, inner meaning opposite to the entry, of the cavity. To fill the cavity with the LPM 113 it is necessary to push out the liquid which was initially in the cavity, for instance blood. Ideally the LPM is injected slowly in a way that it can form a boundary 204 between the liquid material injected and the liquid which was initially in the cavity. A second flow 203 is induced. This flow consists of the initial liquid in the cavity which is leaving the cavity. In case this initial liquid starts to mix with the injected liquid material this cavity-outflow 203 can also consist of a mixture of initial liquid and injected liquid material. In this setting the object 108 is used to control the outflow 203 by leaving an open space 205 between the vessel 101 and the cavity space to be filled 113. In some case the object 108 can also play the role of a plug to close or narrow the entry to the cavity space 114. Such a narrowing 206 is also illustrated. In the image the object 108 is sufficiently elastic to not only narrow the entry of the cavity, but also surround the cannula 110. This prevents leakage of the initial liquid from the vessel 101 into the cavity space 103. One way to achieve such a plugging effect is by pressurizing the object 108. Thus it will push against the wall at a given position 207 and also exert a pressure on the opposite site against the cannula 110 or toward the entry of the cavity. In the present embodiment the inflow 202 and outflow 203 can be induced by pressurizing the injected liquid 103 and applying a certain flowrate. Thus the initial liquid is flushed out of the cavity. Another option is by using an LPM with a lower density. In this case the exit 205 has to be placed downwards. The LPM can be injected slowly and will push down the heavier initial liquid out of the cavity by means of gravitation. In FIG. 5b the opposite situation is presented where the cavity is facing downwards, meaning that its entry and exit 205 are at the top. In this case the LPM is preferably heavier than the native liquid in the cavity to push out the native material at the outflow 203. Also in this case other mechanisms such as the flushing out by injecting a higher amount of liquid material 103 at a higher pressure can be done. Parts of the LMP can leak into the vessel 101. During light illumination the light does not reach the material outside of the sealed cavity.

In another embodiment, the device consists of thin and a thicker catheter. The thinner one is guided within the ticker one. One of them is used to inject the photosensitive material while the other one is used to aspirate or such the liquid which was initially in the cavity.

Figure 6A:
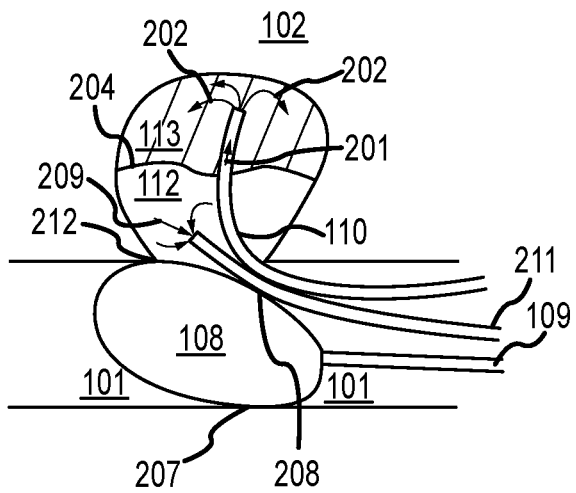
FIGS. 6(*a*) and (*b*) show an injection method including aspiration or outflow catheters.
Figure 6B:
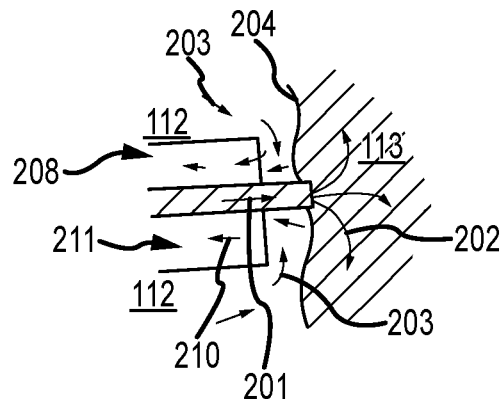

FIGS. 6(a) and (b) show other types of procedure options. In FIG. 6a an arrangement is presented where two cannulas are used, a first cannula 110 to inject the LPM and a second cannula 211 through which the initial liquid in the cavity flows out or is sucked out of the cavity. A flow 209 towards the cannula 211 is induced by positive pressure in 110 or a negative pressure in 211. Thus also in the cannula 211 a flow 210 is induced. By this flow the initial liquid of the cavity is brought away, meaning for example brought out of the body. In this setting the object 108 can be used to completely seal the cavity by pushing against the cannulas 110 and 211 and closing the space 208 between cannula and tissue or by pushing directly against the issue and closing the space 212 between tissue and object 108. Also more than two cannulas can be used, for instance to suck out the initial liquid at different positions or to guide an illumination fiber within a third cannula. Furthermore also multifunctional cannulas are part of the invention. In FIG. 6b an arrangement is shown where a first cannula 110 is situated within the second cannula 211. The LPM 113 flows 201 through cannula 110 and spreads 202 into the cavity, and the initial cavity-liquid flows 203 toward the cannula 211 where it flows out 210.

According to another aspect of the present invention, the optical waveguide of the injection device can include a principal waveguide, or a principal waveguide and light diffusion means or a plurality of secondary waveguides to spatially distribute the electromagnetic radiation propagated by the principal waveguide throughout the photo-activatable substance and organic cavity.

In one aspect, the photocurable material is an implant, filler, tissue replacement, gel or scaffold applied to a living host. In a preferred aspect, the photocurable material is a biomaterial such as photo-responsive hydrogels (containing e.g. Polyethylen Glycol, Hyaluronans, methacrylates and the like), composite hydrogel (including e.g. cellulose fiber), gelatin-agar system, gel based on amino acids sequences derived from proteins, collagen, silk fibers, polyurethane, polycarbonate urethane, cellulose, poly vinyl alcohol or other poly- or copolymers.

Other suitable polymers material include hydrophilic polymers and polymers derived from hydrophilic polymers including hydrogels. Suitable hydrophilic polymers include poly(vinyl alcohol), poly(glycols) such as poly(ethylene glycol) dimethacrylate, poly(ethylene glycol) diacrylate, poly(hydroxyethyl methacrylate), poly(vinyl pyrrolidone), poly(acrylamide), poly(acrylic acid), hydrolyzed poly(acrylonitrile), poly(ethyleneimine), ethoxylated poly(ethyleneimine) and poly(allylamine) as well as, monomers, oligomers, macromers, copolymers and/or other derivatives of the foregoing. Hydrophilic biopolymers and I PNs may also be suitable. Other suitable polymers include polymers of poly (vinyl alcohol), poly(glycols), poly(ethylene glycol) dimethacrylate, poly(ethylene glycol) diacrylate, poly(hydroxyethyl methacrylate), poly(vinyl pyrrolidone), poly (acrylamide), poly(acrylic acid), hydrolyzed poly (acrylonitrile), poly(ethyleneimine), ethoxylated poly (ethyleneimine), poly(allyl alcohol), poly(allylamine), biopolymers such as chitosan, agarose, hyaluronic acid, collagen and gelatin, (semi) interpenetrating network hydrogels, peptide, protein, and blends and mixtures thereof.

In one aspect, photosensitizers sensible in the visible wavelength such as Riboflavin, Rose Bengal, Camphorquinone, phosphorus-based initiators (e.g. BAPO) are used to induce the photochemical reaction. In another aspect photosensitizers in the ultraviolet range such as Irgacure 819 or Irgacure 2959 are used. If necessary the sensitizer can be used with a co-initiator such as amine. Other examples are ITX (4-Isopropyl-9-thioxanthenone), Lucirin TPO (2,4,6-Trimethylbenzoyl-diphenyl-phosphineoxide), Irgacure 184 (1-Hydroxy-cyclohexyl-phenyl-ketone), 1-[4-(2-Hydroxy-ethoxy)-phenyl]-2-hydroxy-2-methyl-1-propane-1-one (Irgacure 2959), phosphine oxide, phenyl bis (2,4,6-trimethyl benzoyl) (Irgacure 819, LAP (lithium phenyl-2,4,6-trimethylbenzoylphosphinate), 7,8-dimethyl-10-((2R,3R,4S)-2,3,4,5-tetrahydroxypentyl) benzo [g] pteridine-2,4(3H,10H)-dione (Riboflavin), 4,5,6,7-tetrachloro-2',4',5',7'-tetraiodofluorescein (Rose Bengal), PL-BDK (Benzil dimethyl ketal), PL-CPK (1-hydroxy-cyclohexylphenyl-ketone) or PL-HMPP (2-hydroxy-2-methyl-1-phenyl-1-propanone).

In one aspect a contrast agent such as Iodine based agents or other agents used in clinics for fluoroscopy, CT-scans or X-ray imaging is mixed to the injected material which allows to image the injected volume from outside of the animal or human body. Thus, the exact position of the material can be identified. Furthermore, leaking material can be traced or holes in tissue or bone can be closed (closed meaning that there is no leakage).

Any combination of the previously mentioned materials, sensitizers, initiators, markers or agents are possible. In a preferred aspect, one or several of the elements or materials described contain a radio-opaque agent or markers (such as, for instance, iodine agents or gold, platinum coating) for safe visualization of the embolic agent and photo-activating device during endovascular delivery under fluoroscopy (i.e punctual or continuous x-ray exposition, magnetic resonance imaging, any type of tomography).

In one aspect the injected liquid is a liquid with a viscosity similar to water (around $10^{-5}$ Pa s), but can also be thicker having viscosities up to 1 Pa s or even higher.

In a preferred aspect, the injected material is hydrophilic and will attract small amounts of water from the surrounding tissues. Thus, it will swell and exert a certain pressure onto the tissue surrounding the cavity. By adapting the amount of hydrophilic molecules within the injected photoactive material the pressure which will be exerted onto the surrounding tissue can be controlled. This pressure is between 1 and 500'000 Pa, ideally between 100 and 10'000 Pa.

The photopolymerized implant is intended to be non resorbable and could be used either in combination with a balloon to protect the parent artery while filling the aneurysm or in combination with a stent to prevent downstream migration of parts of the implant during the solidification process.

Another aspect of the device is to combine the liquid agent with chemical cell-mediated factors such as VEGF (vascular endothelial growth factors), FGF (fibroblast growth factors) or other factors to enhance healing of the aneurysm and promote closure at the neck of the aneurysm and obtain a more stable long-term occlusion through scarring or endothelial remodeling, or to help avoid a condition resulting from a ruptured aneurysm, such as a vasospasm.

Other potential applications concern the combination of the liquid agent directly with autologous pluripotent or endothelial progenitor cells or other types of cells to achieve the same healing purposes.

FIGS. 7(a) and (b) show exemplary snail like illumination options. After injection, the LPM 113, it needs to be activated by light illumination. The light guiding element 111 is in this case a spiral- or snail-like illumination device 301. It's main function is to guide light into the cavity. A second function is to distribute the light properly within the cavity and to illuminate 112 the previously LPM 113 everywhere. At the point 206 where it enters the cavity, it can be guided by a cannula. In FIG. 7b a more coil like light-guiding structure 302 is presented. Element 302 can be used to form several loops within the cavity. This can increase the amount or the homogeneity of light 112 brought to the LPM 113. Furthermore the light-guiding structure 302 can also contribute to structural properties of the injected material after photoactivation, for instance making it stiffer or tougher.

FIG. 8 depicts a tree-like illumination option. In this arrangement the light guide 111 consists of a main light guiding element 303, comparable to a trunk, and secondary light guiding elements 305, comparable to branches. At an intersection 304 the light is coupled from the main element 303 into the branches 305. This can be done by direct physical contact. It is also possible to use glue, an index matching liquid or another intermediate object which guides the light from 303 to 305. It is also possible that the light guiding element 111 is one single object which is treated or designed in a way to have two different sections 303 and 305. The light 112 can exit the element 305 at any position, for instance at a precisely defined position in the middle, at several positions along the element or simply at its distal end.

FIG. 9 depicts an illumination option where the light guide 111 has a modified tip 311. The illustrated tip is a side-firing tip where the light 112 is emitted laterally. Other type of tip options such as diffuser, wherein said diffuser is a tip which sends the light into every direction in an arbitrarily or structured way, can be used. This deviation in light can be achieved by machining the fiber mechanically, by ablation using a high power light source, by an chemical etching process, a deposition of a material such as an aluminum coating or any other type of surface or material treatment. The goal of this treatment is to change the path of the photons guided in 111 to illuminate the LPM 113.

According to another aspect of the present invention, the injection device is configured to confine the electromagnetic radiation provided by the waveguide inside the organic cavity and/or prevent the photo-activation of the photo-activatable substance outside the organic cavity.

The device is further configured to confine the photo-activatable substance inside the organic cavity and prevent further substances entering the organic cavity during photo-activation of the photo-activatable substance.

According to yet another aspect of the present invention, the injection device can include a catheter integrated into the balloon and through which the injection cannula and/or the optical waveguide is introduced into the organic cavity.

In a preferred aspect, an inflatable balloon is used to block the access to the tissue cavity. For instance in case of an aneurysm the balloon blocks the blood flow in the arterial or venous system. Thus the injected photoactive material cannot be pushed out of the aneurysm cavity during photoactivation.

In one embodiment, a balloon filled with dark (light absorbing) liquid is used to avoid light transmission through the balloon and avoid polymerization of the photosensitive material inside the parent artery (risk of arterial occlusion).

In another embodiment, the balloon consists of a light absorbing material and the light is directly absorbed by the balloon.

In one embodiment, the balloon is filled with mirror-like liquid (including for instance aluminum-, gold-, titanium-, silver- or ceramic-based particles) to refract all the light back inside the aneurysm and increase the illumination of the photo-sensitzing agents of the liquid embolic agent by reflection.

In another embodiment, the balloon is coated with a reflective material such as aluminum to reflect the actinic light back into the cavity.

In one embodiment, the device includes one or several catheters to flush a liquid, such as blood, out of the cavity and then inject a photosensitive material.

In one embodiment, a balloon which changes its size according to the geometry of the blood vessel is disclosed. The balloon can be filled at different levels (i.e. different pressures or different amounts of injected liquid). Thus, it can be tuned to different states in which it occults partly or entirely the entrance to a tissue cavity, such an aneurysm. In a partly inflated state injected liquid can leave the cavity and thus the pressure within the cavity is kept at a constant level. In a completely inflated state the cavity entrance is blocked by the inflated balloon.

In one embodiment, the inflatable balloon with a cylindrical shape changes its size along its longitudinal direction. Thus, it can act as a valve to close the entrance of a tissue cavity connected laterally to a cylindrical cannel while being inflated. Such a balloon can have an end with a stiffer and another end with a softer wall. Thus it inflates first on the soft end and then on stiffer side.

Figure 10:
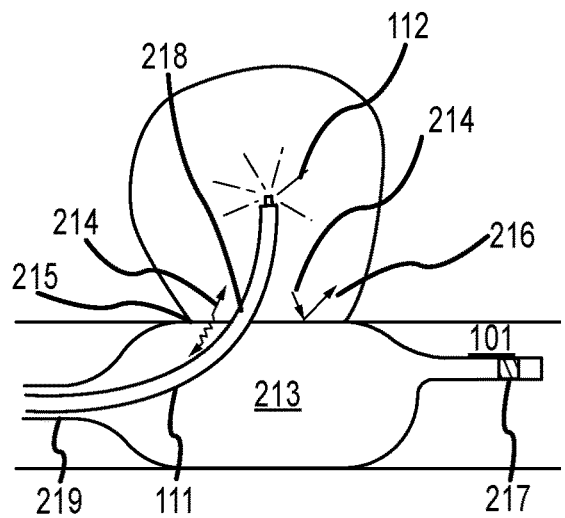
FIG. 10 shows a balloon which is able to block the light emitted within the tissue cavity and thus avoids that actinic light can reach the vessel.

FIG. 10 shows a balloon which is able to block the light 112 emitted within the tissue cavity and thus avoids that actinic light can reach the space 101 where it might irradiate residues of injected LPM 113. Two examples of light blocking are disclosed: In one embodiment the balloon is filled with an absorbing biocompatible liquid such as a black dye dissolved in a solvent such as water. A photon or light irradiation 214 will be imping on the balloon. If the balloon is transparent or partially transparent, 214 will cross the interface be absorbed 215 by the absorbing liquid. In another embodiment the balloon is made out of a light absorbing material such as black rubber and 214 will be absorbed directly by the balloon. In another embodiment, the balloon 213 is coated inside or outside with a reflective coating (for instance aluminum, gold, ceramic, titanium or silver based) thus 214 will be entirely or partly reflected 216 and propagate back into the tissue cavity. Instead of a coating, reflective particles suspended in a solvent can also be injected into the balloon when inflating it which will also result in a reflection of light back into the tissue cavity. Furthermore, the balloon light confining balloon also comprises solid markers at the distal or proximal end or in between (217 is an example of such a marker), but also includes markers such as for example Iodine containing molecules which can be added to the absorbing, reflecting, opaque or transparent liquid inside 213. The catheter 111 may be directly integrated into the balloon. It can be attached (e.g. mechanically or glued) to the balloon at a position 218 at a defined distance from the distal tip of the catheter 111. At the proximal end of the balloon the catheter may be guided inside the balloon catheter 219. It can also be integrated into balloon wall as for position 218. More than one catheter 111 may be integrated into the balloon. To place the catheter 111 into the tissue cavity a guide wire (not shown, but well known in the state of the art) is used. At the same time the non-inflated balloon 213 is dangling in vessel 101. It can then be gradually inflated to reach its final position presented in the FIG. 10.

According to another aspect of the present invention, the balloon of the injection device is configured to be incrementally inflated by predetermined volume amounts to control the removal of a resident substance from the organic cavity and prevent removal of the non-activated photoactivatable substance from the organic cavity.

Figure 11:
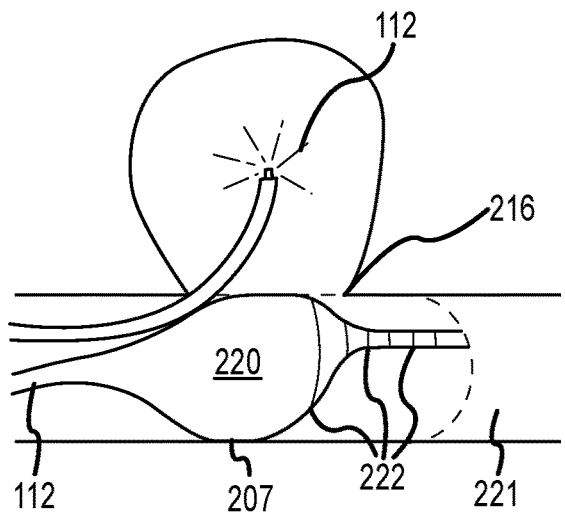
FIG. 11 presents a light reflecting or absorbing balloon.

FIG. 11 shows a light reflecting or absorbing balloon 220 which can gradually seal a tissue cavity 103 physically (no exchange or only controlled exchange of material between 101 and 103) and optically (no light emitted 112 in the cavity 103 can reach the vessel 101). In this aspect the direction of deformation of the balloon during inflation is controlled. For instance the balloon is inflated in a linear direction staring on a proximal side (220) and then expanding towards a distal side until it reaches its final geometrical form 221, which in this case seals the cavity by pressing against the walls of the artery (206, 207). Such a balloon is designed by coating or applying supplementary layers onto the balloon in a strip like fashion 220 which will results in a higher mechanical resistance and thus later inflation. The strips 220 can be arrange in different directions. Also other geometries different to trips can be applied. For instance a balloon can be made out of nylon and then be coated with polyethylene terephthalate strips. Other materials such as polyvinyl chloride, other polymers or materials used to fabricate balloons for cardiovascular surgery can be used. Beside strips or layered coatings a balloon with different thicknesses can be designed which also results in a non-homogeneous inflation pattern. These different thicknesses are for instance achieved by heating up certain parts of the balloon at different temperatures during a blow molding production of the balloon.

Figure 12:
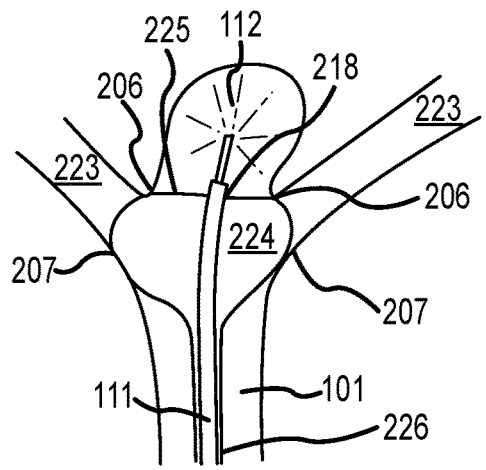
FIG. 12 discloses a reflective balloon for vessel bifurcations.

FIG. 12 discloses a more circular or pear shaped balloon 224 to seal off a tissue 103 cavity from blood flow in 101 or light 112. The balloon is used during a photo-activation of a LPM in tissue cavity 103 close to a vessel bifurcation (principle vessel 101 and secondary vessels 223). The balloon is attached to the catheter 111 at a position 218. The emitted light 112 will impinge onto the surface 225 of the balloon. It can be absorbed or reflected. During inflation the balloon will press against the vessel walls at 206 and 207. Catheter 111 and balloon 224 can be guided within the same main catheter 226 or two or more catheters.

Figures 13A, 13B:
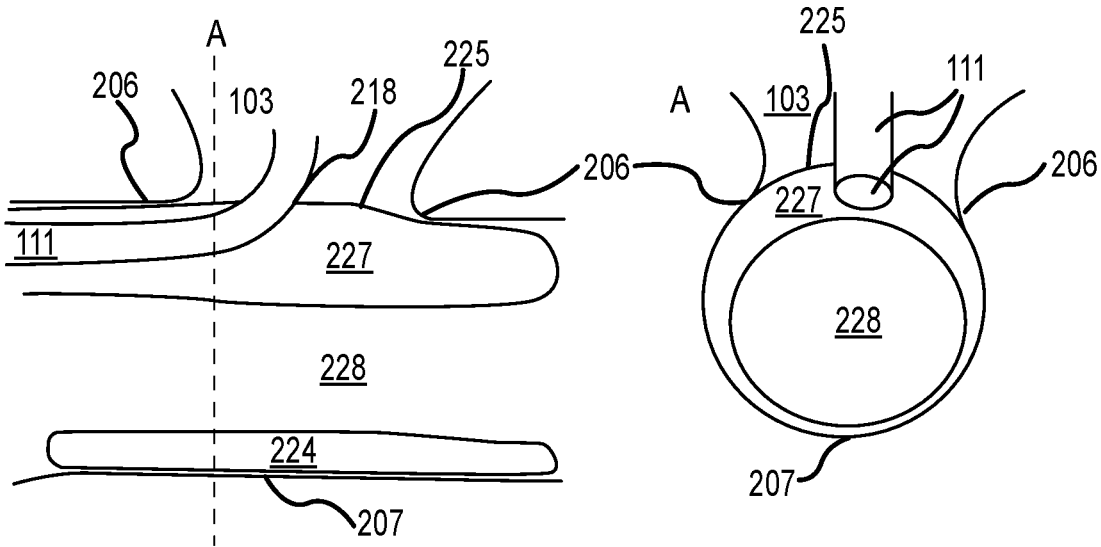
FIGS. 13(*a*) and (*b*) present a reflective balloon which does not hinder blood flow.

FIGS. 13(a) and (b) present a reflective balloon 227 which does not hinder blood flow. It contains a cannula 111 which may be used for injection of LPM and/or go guide a light guide into the cavity 103. 111 is integrated 218 into the inflatable balloon 227. It has a reflective or absorptive surface 225 or is filled with a liquid reflecting or absorbing light. The inflatable balloon has a cylindrical shape which permits to not obstruct the blood flow within 101. The blood is guided within balloon in a lumen 228 formed by the balloon. It closes the tissue cavity at 206. It touches the vessel wall at one or several positions (207) which induces a pressure to close the tissue cavity 103. The balloon is inflated through a catheter 226 (not shown) which is connected to the balloon at any position of the cylinder. "A" is a transversal cut to better illustrate the cylindrical shape of the balloon.

In one aspect the light guiding element can consists of two materials. The first material is shaped in an elongated structure and surrounded in radial direction by the second material. The light is guided by total internal reflection. Thus, the refractive index of the first material is higher than the refractive index of the second material. For instance the first material can be the core of an optical fiber and the second material the cladding.

In a preferred aspect the first material is a solid material with a refractive index higher than the second (e.g. above 1.4 such as glass or PMMA) and the outer material a liquid or solid material with an index of refraction lower than the first material (for instance water-base polymer or hydrogel). In this aspect the inner material has a diameter smaller than 500 µm, or preferably smaller than 100 µm or even more preferably smaller than 20 µm. In this aspect the second material can be activated by light.

Figure 14:
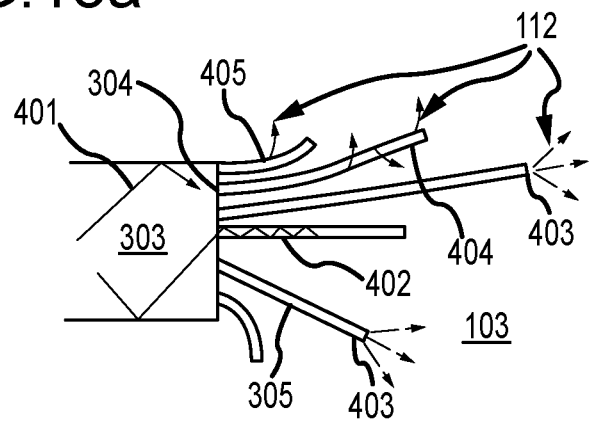
FIG. 14 shows optical guiding and scattering of the light between a main light guide and secondary light guides.

FIG. 14 shows optical guiding and scattering of the light between a main light guide 303 and secondary light guides 305. A photon 401 guided in the primary light guide crosses the interface 304 which assures the mechanical and optical contact between 303 and 305. It is then guided in 305 which is represented as 402. The guiding of the photon is achieved by an immediate or gradual radial-change in refractive index. For example 303 or 305 can consist of a core with a higher refractive index and a cladding with a lower refractive index (lower in respect to the core). The simples example of 303 couple light into 305 are tow optical glass fiber which are butt-coupled to each other, wherein butt-coupled means that the distal end of 303 is placed against the proximal end of 305 and kept in place by a physical contact between both of them or surrounding them radially. The interface 304 can simply consist of a gas such as air, a liquid for instance water or a solid for instance glass as long as it transmits the photons 401 or light 112 required to activate the LPM 113. Ideally 304 also holds together 303 and 305 while transmitting the photon 401. Such an example of 304 is an index-matching glue (e.g. Norland Optical Adhesives). In the simples example, where 305 is a standard optical fiber the light is guided to its proximal type 403 and emitted to illuminated 113. Another example is 404 where the light 112 is emitted at several positions between the proximal and the distal tip of 305 to illuminated 113. Yet another example is 405 where the light is emitted at specific positions between the proximal and the distal tip of 305.

Figure 15:
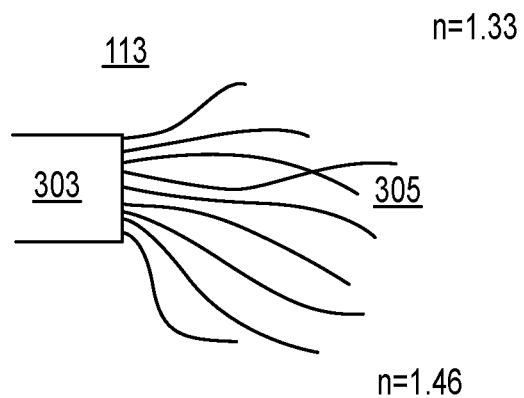
FIG. 15 is a design where the light is also guided by the surrounding material.

FIG. 15 is a design where the light is also guided by the surrounding material, wherein this surrounding material can for instance be the material which was initially in the cavity or the LMP 113. This material has lower refractive index then the light guiding element 305. This allows the light 402 to be guided within 305. For example 305 has a refractive index of approximately 1.46 and 103 a refractive index of approximately 1.33.

Figure 16:
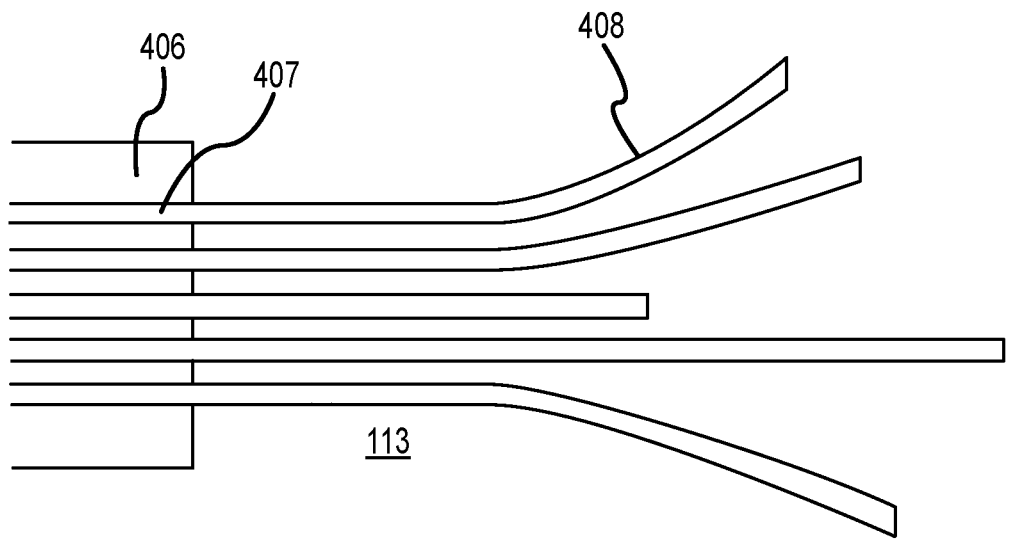
FIG. 16 is a design including a multicore fiber.

FIG. 16 is a design where the light guide 111 consists of a proximal and a distal part which are not separated by an interface 304. The proximal part consists of an element 407 and an element 406 which surrounding 407. The element 407 continues into the distal part of 111. In the distal part of the element 407 is not anymore surrounded by element 406 and can freely move in space 408. This design can for instance include a multicore fiber. In this example the light guide 111 is directly replaced by a multicore fiber. The cladding 406 and the cores 407 allow the transmission of the light within the different cores. In the distal part of 111 there is no more cladding and the cores 408 are not surrounded by 406 anymore. In this example the light is guided by a discrete or gradual change of index between 406 and 407, and by a discrete or gradual change of index between 408 and 113.

According to yet another aspect of the present invention, the injection device includes means for injecting a plurality of scattering particles into the organic cavity to diffuse the electromagnetic radiation provided by the optical waveguide throughout the photo-activatable substance and organic cavity.

Figure 17:
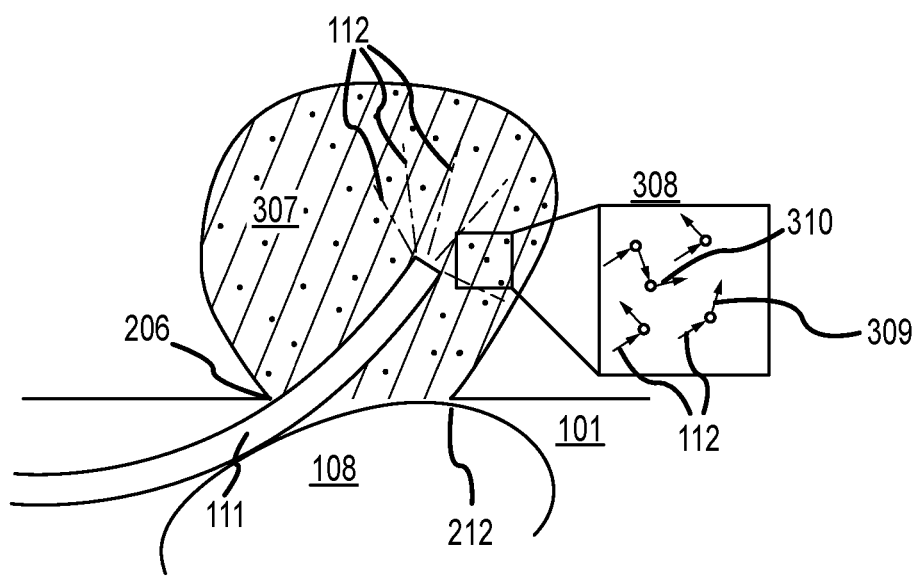
FIG. 17 is a design where the light is scattered using scattering particles mixed to the injected material.

FIG. 17 is a design where the light is scattered by scattering particles 307 mixed to the injected material. Thus the light 112 emitted by 111 can be scattered. Such a scattering event 309 is shown it the detailed view 308. Multiple scattering events 310, where a photon is scattered more than once are possible. The goal of these scattering particles is to distribute the light within the cavity. Thus the cavity can be illuminated in a more uniform way or the light 112 can reach spots which would otherwise not be possible to reach. These particles can consist of any type of scattering material. Typically their scattering coefficient is higher than their absorption coefficient, ideally by at least one order of magnitude. An example of such scattering particles are fat emulsions such as Intralipid, Lipovenoes or Clinoleic at different concentrations.

FIGS. 18(a), (b) and (c) are more detailed descriptions of primary 303 or secondary fibers 305 or their tips. These tips can also apply to primary light guides 111. 402 are photons guided within 305 and reflected at the position 405 by total internal reflection until they reach the distal of 305. FIG. 17a shows 305 with defects 406 inside. These defects can consist of particles which redirect the light. They can also simply be gas bubbles inside the light guide or other structural changes within the light guide affecting the direction of a photon 402 and redirecting it 407, which leads to illumination 112 of the material 113. In the second example in FIG. 17b this distal tip 409 consists of a holographic grating which will redirect the photon 402. Distal tip 409 can redirect all of the light or only part of it. It can refract certain wavelengths and not affect others. In FIG. 17c a tip 305 is presented with several gratings 408 along the light guide are introduced. These gratings refract part of the light and transmit others which leads to a sideward illumination 112 of the material 103. A further example of a secondary fiber tip is a material is a diffusing which is attached to the 303 in liquid form. For instance a drop of glue (e.g. Northland Optical Adhesives) containing scattering or reflective particles (e.g. aluminum enamel) is applied onto the tip and then cured. This results in a type of "disco ball" illumination at the fiber tip.

FIGS. 19(a) and (b) illustrates a solidified LDP 501 after illumination. The object 108 is taken away and a boundary 502 between 501 and 101 is formed. At this point the light guide 111 is still inside the cavity. In one embodiment 111 is simply pulled out of 501. In this case the adherence of the material 501 to the tissue 102 is higher than the adherence between the light guide 111 and the material 501. Ideally 111 does not adhere to 501 or only sticks to it slightly or weakly. Thus 111 can simply be pulled out (503) from the material 501.

In yet another aspect of the present invention the injection device includes a detachment mechanism to detach the plurality of secondary waveguides from the principal waveguide to permit the plurality of secondary waveguides to permanently remain inside the organic cavity.

In another embodiment part of the light guide 111 stays inside the cavity. In this case the light guide 111 needs to be separated or cut into pieces at a position 504 close to the interface 502. This cut or local destruction of 111 can take place anywhere between its proximal and distal end. It can for instance be introduced on the interface 304 between 303 and 305. This cut can be introduced into 111 externally by a mechanism or tool brought close to 504. For instance the cannula 110 can be used to disrupt 111. To do this any mechanism inducing a local destruction or cut of 111 is imaginable including an electrical current which for instance melts a part of 111 at 504, an electrical current which changes the material properties of 111 at 504 for instance making it fragile, an electromagnetic wave which changes the material of 111 at 504 for instance heating it up, a mechanical strain or/and stress which is introduced or induced at 504, a change in material or cut which is generated by acoustic waves which change the material at 504 or a cyclic or punctual mechanical load applied to 504. In one embodiment a fissure or defect is introduced at 504 previously to control the position 504. An example is a small fissure carved around 111. After illumination and during removal a bending or torsion moment or/and shear or compressive force is applied to 111 by deforming 110 accordingly. This moment or force breaks 111 at 504. To induce the previous mechanisms at 504 one option is to place one or several elements 505 at the tip of 111. This element can consist of one or several electrodes, electric wires, optical light guides or mechanical objects such as clamps. This element can be controlled from the outside, wherein outside is a position close to the proximal end of 110 or 111. The elements 505 can be integrated or added to the catheter 110. They can partially or completely induce the breakage or cut of 111 at 504.

In one preferred aspect, the small thickness of the light guiding element allows it to be coiled or placed in a round, spiral, elliptic or also chaotic manner inside the tissue cavity.

In another preferred aspect, the light guiding element consists of a flexible easily bendable material (in the range of other commercially available coils for aneurysm treatment) which will allow coiling within a tissue cavity.

In another aspect, a coating is applied to the light guiding element to induce such coiling (for instance a soft coating on one lateral side and a stiffer coating on the opposite side; or a coating containing a pre-stress is place on one lateral side). Such a coating may, but does not have to transmit or reflect light.

In one aspect, the light guiding element is a coil. Coil meaning having the structural properties similar in shape than the coil usually used to fill aneurysm.

In one aspect, the light guiding element is combined with existing coils. In another aspect existing coils are coated with a reflective coating. Which is able to further distribute the light within the tissue cavity. In another aspect the coils do not only reflect light but can also diffuse, refract or transmit it.

In one aspect the light emitting coil consists of an flexible material or polymer such as PMMA. Flexible meaning that it can be coiled up to sub-centimeter structure while still transmitting light.

Figure 20:
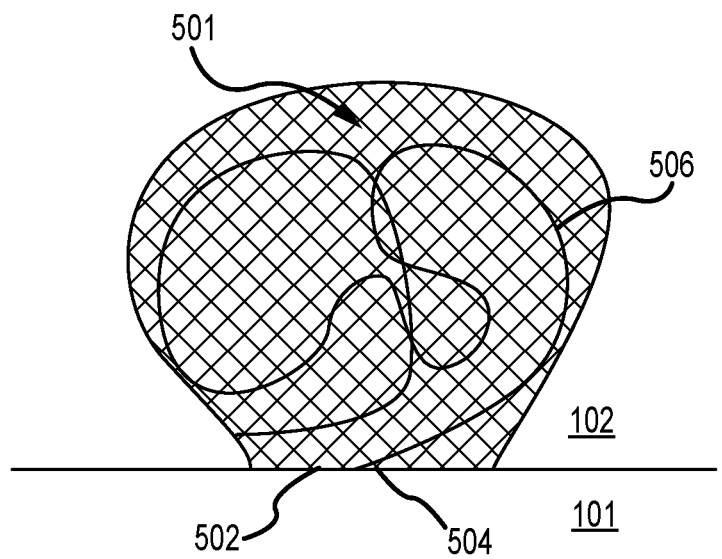
FIG. 20 illustrates an example of a primary or secondary fiber left as a coil in the aneurysm.

FIG. 20 illustrates an example of a fiber left as a coil in the aneurysm. Once the distal part of 111 is detached by cutting it at the position 504, a part 506 of the light guide 111 remains inside the hardened or activated material 501. The goal of 506 is on one side to strengthen the material 501 statically. It also helps to prevent any displacement of material 501 towards the vessel 101. Thus, it also stabilizes 501 and keeps the boundary 502 in place. In a further embodiment 501 can attract particles or fluid volumes from the liquid within 101 or also from the tissue 102 to exert an external pressure towards the tissue 102 or eventually also towards the vessel 101. An example for such a mechanism is an osmotic reaction. For instance the material 501 could attract water from 101 or 102 to increase its own volume and exert a pressure onto the boundaries of the tissue cavity. 506 can also increase, decrease or stabilize such a pressure.

In one aspect, the illumination element consists of one optical fiber or several fibers which may be connected between each other. This physical connection can be achieved by butt-coupling the fibers using a glue or another element to connect them. This physical connection can be undone remotely by means of electromagnetic radiation, electrical current or mechanical stresses or strains. Thus, in this aspect the light guiding element consists of several parts, some of them, situated at the distal end, are detachable and remain inside the body after detachment. The other parts, situated at the proximal end, are retrieved after detachment.

In one aspect different light sources are used, either to activate the injected photoactive material or to detach the detachable parts of the light guiding element. It this aspect also different sub-parts of the detachable parts can react to different wavelengths. For instance a laser at 10600 nm is used to detach a first part of light guiding element and a second laser at 1523 nm is used to detach a second part of the light guiding element.

In one aspect, the light-guiding element is selected from the group of beam splitter, band-pass filter and Bragg grating.

In one aspect, the light sources emit light within a wavelength range of 200-700 nanometers for photo-activation and within a wavelength range of 150-10700 nanometers for detachment.

The detachment mechanism can be for example configured to be activated using electromagnetic radiation of a different energy to that used to activate the photo-activatable substance.

Figure 21:
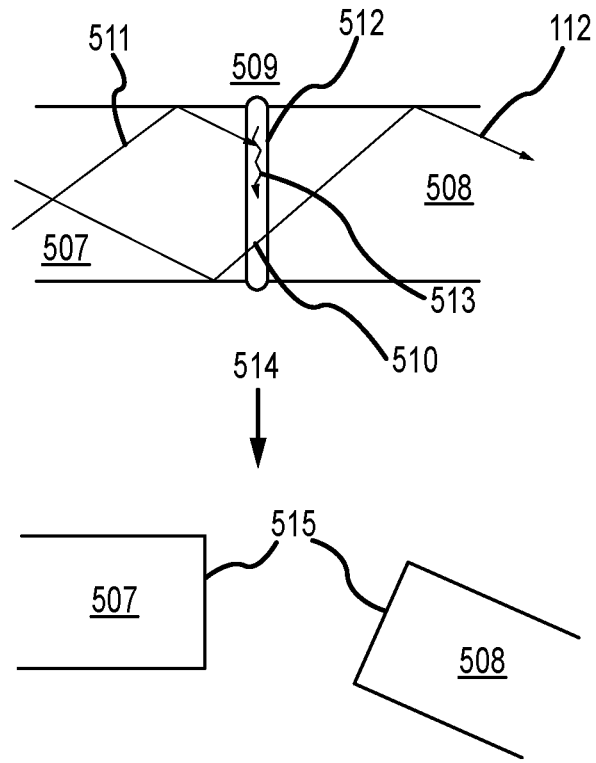
FIG. 21 illustrates the illumination, and detachment mechanism using an illumination at different wavelength.

FIG. 21 illustrates the light guide 111 during illumination and detachment mechanism using an illumination at different wavelength. To activate the LPM 113 actinic light 112 is guided through the light guide 111 from its proximal to its distal end. To split the light guide 111 into a proximal 507 and a distal part 508 as for instance in the case where the distal part 508 (506) is left inside a cavity, a layer or intermediate piece 509 is placed between 507 and 508. This layer is transparent 510 (more than 90% of 112 is transmitted) or otherwise at least transparent enough to induce the reaction of 113 at the distal tip of 111. To detach 508 from 507 or cut 111 at the position 504 a second light source is placed at the proximal end of 111 or guide into 111. The light 511 of this second light source might have a different intensity than 112 or a different wavelength. The light or the photons 511 are completely or partly absorbed on the intermediate layer 509, wherein the photon has a certain energy according to Planck's relationship and wherein the absorption of a photon is the process of the photon being absorbed by the molecules, atoms or lattice or structure build by molecules of the material 509 and wherein this processes requires that the photon energy given by the Planck relationship or a multiple of this energy is equal to the energy separation of the participating pair of quantum energy states. On the macroscopic level the absorption of a photon can result in heat and thus in an increase in temperature 513 of the material 509. This increase in temperature 513 can entirely or partly destroy the material layer 509 and will lead to a separation 514 of 507 and 508. The speed of this process can be tuned and depends on the intensity of 511. It can occur within some seconds or minutes, ideally it takes less than one second. An example for 509 is Norland's optical adhesive No. 60, 507 could be an infrared transmitting optical fiber (e.g. Amorphous Materials Inc.) and 511 a frequency doubled CO2 laser with a wavelength between 5 and 7 µm. In another embodiment, the absorbed photons change the energy levels of electrons which then trigger the chemical reactions by creating free radicals, cations or anions, which changes the material properties of 509. This change in material leads to the rupture 514 or a weakening of 509. In one embodiment 509 consists of a photoresist (such as those commonly used in photolithography) layer which is degenerated upon illumination. In another embodiment, the previous described rupture mechanisms is combined with other described mechanisms for instance a bending of the guide 110. After the separation 514 the parts 515 of the material 509 may remain on the 507 or 508. It is also imaginable that they completely disappear or are dissolved within the environment for instance the fluid within 101.

Figure 22:
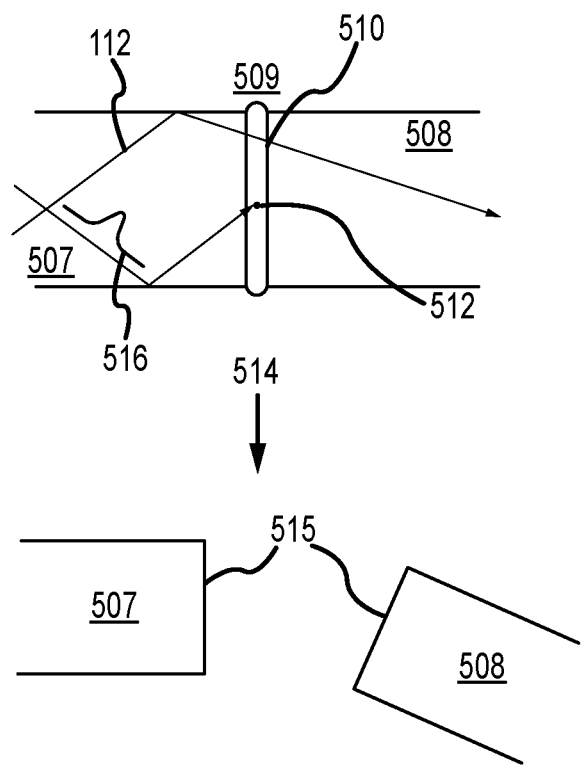
FIG. 22 illustrates the detachment mechanism using a pulsed light source.

FIG. 22 illustrates the detachment mechanism wherein the illumination light 511 is a pulsed light source 516. The electromagnetic wave or photons 516 is absorbed 512 which leads to a rupture 514. In one embodiment the light 112 and 516 are the same pulsed coupled energy field with the same wavelength. In this case 509 transmit the light 112/516 at its wavelength. Yet, by increasing the intensity of 112/516 non-linear effects for instance two-photon absorption on 509 become important. Thus, by increasing the intensity of 112/516 a threshold for a non-linear effect is reached or, as the effect itself is non-linear, a linear increase of intensity leads to a non-linear increase of, for instance, absorbed power on 509. For example at an illumination power of 1 mW the absorbed power is 0.01 mW and the heat to be evacuated 0.005 mW, and at 10 mW the absorbed power is 1 mW and the heat to be evacuated is 0.5 mW which leads to a rupture 514 of 111.

The method and device can be used for any type of aneurysm or tissue cavity geometries. Round shapes, elongated, shared, heart or any other type shapes are imaginable. The size of the filled cavities can range from one 1 mm in diameter to 5 cm. In case of an elongated cavity, the size can increase up to 20 cm. Also the neck of a cavity (the space at the entrance of a cavity) can be of different shapes or sizes. Usually, the cavity is closed in a flat manner, but also other types of taps can be formed using a balloon, a stent or another occlusion devices during photopolymerization. Also the vessels connected to the cavity can have different shape. A cavity can be situated at a bifurcation of two vessel or can also be situated on the wall of another cavity, such as for instance the heart.

In a preferred aspect, the injected photo-active material sticks to the tissue cavity after photoactivation. It may also present good adherence to a detached part of the light guiding element (for instance by physical integration). But it may also be designed in a way that it doesn't stick to retrieved part of the light guiding element (for instance a water-base polymer which doesn't adhere well to a glass surface of the distal tip of a light guiding element).

Figure 23:
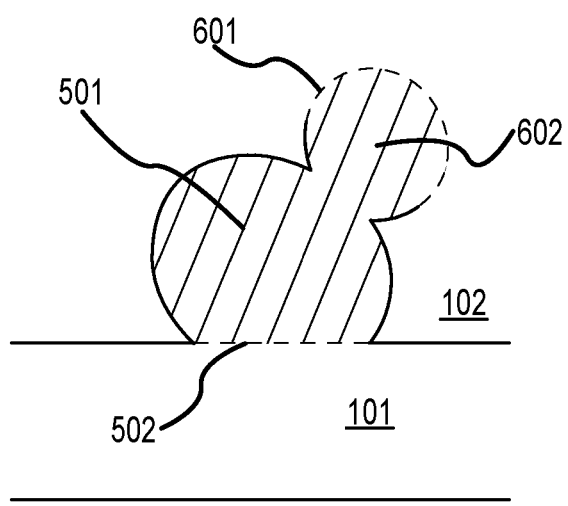
FIG. 23 illustrates a repaired aneurysm after rupture.

FIG. 23 illustrates a repaired aneurysm after rupture. In one embodiment the device and method can be used to repair ruptured aneurysms. In this case the filled and polymerized volume after surgery consists not only of a main cavity 501, but also of a secondary cavity 602. This secondary cavity might have been induced previously by a rupture or destruction of the interface between cavity 103 and tissue 102. In at least one embodiment this secondary cavity is filled with the same initial fluid as 101 and fills the volume within 501 and 602 and delimited with the boundary 601. In this case the volume 501 and 602 are emptied and replaced completely or partly by the injected material. In at least one embodiment the injected material acts as a sealant of a vessel, cavity or rupture volume, wherein rupture volume is a closed volume where one or several holes were introduced or its walls broke resulting in holes.

The main treatment indication for the current invention would be directed towards the endovascular cure of cerebral aneurysms. Aneurysms located elsewhere and other conditions also amenable to endovascular treatment, however, such as hypervascular tumors or abnormal communications between arteries and veins (called fistulas or arterio-venous malformations), as well as venous conditions such as varicose veins, can also be treated with the current invention. Likewise, other non-vascular organic cavities can be treated with the current invention.

One of the most fundamental properties of the photopolymer is to enhance the mid and long term stability of the aneurysm occlusion while minimizing the inflammatory and prothrombotic reactions at the interface between the implant and blood. This could be achieved by adding surface molecules to the hydrogel (such as diisocyanate) capable of limiting platelet activation to reduce the risk of acute or delayed artery thrombosis and prevent intra-sacular clot remodelling and modification of the implant, such as seen with other intra-sacular implants like coils.

When applied on living organisms such as animals, including human beings, a particular aspect of the invention relies in a method of replacing, healing or otherwise treating a damaged or altered organ or tissue in a living host by precisely injecting a photosensitive material, preferably in a minimally invasive way, to a target body site through the above-described method.

In one aspect, therefore, the tissue or cavity is a body tissue or body cavity. In a preferred aspect, the body tissue or body cavity is from an animal, including human beings. In a particular aspect, the method further comprises the step of introducing the applicator inside the animal body through surgical means or through an orifice. In at least one embodiment, the device and methods of the invention are used for injection and photopolymerization of materials to treat aneurysms. In this case the aneurysm is filled with liquid photocurable material to stop blood flow within the aneurysm cavity.

In at least one embodiment, the device is used to activate on embolic liquid agent which will clot a blood vessel or cavity.

In at least one embodiment, the device and method are used to seal a vein, for instance to treat varices. In one aspect the disclosed method and device is combined with other solid or liquid intra or extra-sacular devices currently available on the market (balloons, stents, coils, WEB, LUNA, etc.).

In one embodiment, the device consists of a further catheter to inject another radio-opaque marker to also monitor the blood flow while performing the injection of the photo-active material or while illuminating the photoactive material. This catheter is not placed within the tissue cavity.

In at least one embodiment, the device and methods of the invention are used to replace completely or partly an organ such as part of the intervertebral disc.

In at least one embodiment, the device and methods of the invention are used to replace, heal or strengthen cartilage tissues such as the articular cartilage of any joints or non-hyaline cartilage.

In at least one embodiment, the device and methods of the invention are used in dental applications such as for instance the injection and hardening of dental cement or hydrogels/composite hydrogels in a minimally invasive way.

In at least one embodiment, the device and methods of the invention are used for cosmetic and esthetic surgery procedures. This could be augmentation mammoplasty or a treatment of glabellar lines by an injection similar to a treatment with Botulinum toxin A or hydrogel.

In at least one embodiment the invention relates to a method to inject, fix or otherwise position a photosensitive material comprising a drug or a pro-drug into or onto a cavity or a tissue in a controlled manner through the device of the invention. This could be for instance surgical methods to treat e.g. cancer where a material containing a (pro-)drug is placed close or into the cancerous tissue. The illumination with actinic light provided by the device is used to fix the material at a given location. In another embodiment the light photoactivates the drug as for example in phototherapy.

Yet another aspect of the present invention relates to an organic cavity injection method including injecting, using an injection cannula, a photo-activatable substance inside an organic cavity; controllably removing, using a balloon, a resident substance from the organic cavity and preventing removal of the non-activated photo-activatable substance from the organic cavity; and providing electromagnetic radiation inside the organic cavity to the photo-activatable substance to photoactive the photo-activatable substance inside the organic cavity.

Providing electromagnetic radiation inside the organic cavity includes inserting an optical waveguide inside the organic cavity to directly place the optical waveguide in contact with the photo-activatable substance to achieve effective and fast photo-activation.

The optical waveguide is preferably inserted inside the organic cavity to substantially fill the organic cavity and enclose the entire outer surface of the optical waveguide portion present in the organic cavity in the photo-activatable substance.

The optical waveguide may include a principal waveguide and a plurality of secondary waveguides to spatially distribute the electromagnetic radiation propagated by the principal waveguide throughout the photo-activatable substance and organic cavity.

The optical waveguide or the plurality of secondary waveguides may be detached to permanently leave the optical waveguide or plurality of secondary waveguides inside the organic cavity.

The detachment can be activated using electromagnetic radiation of a different energy to that used to activate the photo-activatable substance.

Light diffusion means or a light diffuser can be provided to diffuse the electromagnetic radiation provided by the optical waveguide throughout the photo-activatable substance and organic cavity to achieve effective and fast photo-activation.

A plurality of scattering particles can be for example injected into the organic cavity to diffuse the electromagnetic radiation provided by the optical waveguide throughout the photo-activatable substance and organic cavity to achieve effective and fast photo-activation.

The balloon can be incrementally inflated by predetermined volume amounts to control the removal of a resident substance from the organic cavity and prevent removal of the non-activated photo-activatable substance from the organic cavity.

The electromagnetic radiation provided by the waveguide is confined inside the organic cavity and/or the balloon to prevent the photo-activation of the photo-activatable substance outside the organic cavity.

The photo-activatable substance is confined inside the organic cavity and further substances are prevented from entering the organic cavity during photo-activation of the photo-activatable substance.

Having described preferred embodiments of this invention, it will be apparent to one of skill in the art that other embodiments incorporating its concept may be used. This invention should not be limited to the disclosed embodiments, but rather should be limited only by the scope of the appended claims.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

What is claimed is:

1. A system for treating an organic cavity containing a resident substance, the system comprising:
a photo-activatable substance, the photo-activatable substance having a non-activated state and an activated state, the photo-activatable substance being solidified in the activated state by electromagnetic radiation and the photo-activatable substance being an inert, biocompatible liquid in the non-activated state;
an injection cannula configured to inject the photo-activatable substance inside the organic cavity;
at least one element configured to control flow of a resident substance from the organic cavity and simultaneously prevent flow of the photo-activatable substance, when the photo-activated substance is in a non-activated state, from the organic cavity;
an applicator configured to guide and place the at least one element in front of the organic cavity;
an optical waveguide inside the injection cannula and configured to emit the electromagnetic radiation inside the organic cavity to the photo-activatable substance to change the photo-activatable substance into the activated state inside the organic cavity, the optical waveguide being configured to be placed inside the organic cavity via the injection cannula or a further cannula;
wherein the photo-activatable substance comprises a photopolymerizable or photocurable material, and the at least one element configured to reflect or absorb the electromagnetic radiation provided by the optical waveguide inside the organic cavity, and
wherein the control of flow of the resident substance is active on/off control of flow out of the organic cavity.

2. The system according to claim 1, wherein the at least one element configured to control the flow of the resident substance from the organic cavity and simultaneously prevent removal of the non-activated photo-activatable substance from the organic cavity includes one or more of the following elements: a balloon, a stent, a flowdiverter, a deployed mesh-like three-dimensional structure, an element increasing or decreasing the hydrostatic pressure in the aneurysm, an element inducing fluid suction or propulsion.

3. The system according to claim 1, wherein the optical waveguide includes a principal waveguide and a plurality of secondary waveguides to spatially distribute the electromagnetic radiation propagated by the principal waveguide throughout the photo-activatable substance and organic cavity.

4. The system according to claim 3, further including a detachment mechanism to detach the plurality of secondary waveguides from the principal waveguide to permit the plurality of secondary waveguides to permanently remain inside the organic cavity.

5. The system according to claim 3, wherein the optical waveguide is integrated into the injection cannula or is part of the injection cannula.

6. The system according to claim 1, further including means for injecting a plurality of scattering particles into the organic cavity to diffuse the electromagnetic radiation provided by the optical waveguide throughout the photo-activatable . substance and the organic cavity.

7. The system according to claim 1, wherein the at least one element is a balloon configured to be incrementally inflated by predetermined volume amounts to remove the resident substance from the organic cavity and prevent removal of the non-activated photo-activatable substance from the organic cavity, the balloon being elastic and configured to surround the injection cannula.

8. The system according to claim 7, wherein the balloon is further configured to confine the electromagnetic radiation provided by the optical waveguide inside the organic cavity and the balloon is configured to prevent the photo-activation of the photo-activatable substance outside the organic cavity, the optical waveguide having a diffuser.

9. The system according to claim 7, wherein the balloon is further configured to confine the photo-activatable substance inside the organic cavity and prevent further substances from entering the organic cavity during the photo-activation of the photoactivatable substance.

10. The system according to claim 7, wherein the injection cannula and the optical waveguide are integrated into the balloon.

11. The system according to claim 1, wherein the at least one element is a balloon filled with a reflective or absorptive solution,
wherein a direction of deformation of the balloon is controlled,
wherein the balloon is configured to allow controlled exchange of the photo-activatable substance between the organic cavity and a blood vessel, and
wherein the balloon is elastic and configured to surround the injection cannula.

12. The system according to claim 1, wherein the at least one element is a balloon coated with a reflective material,
wherein a direction of deformation of the balloon is controlled,
wherein the balloon is configured to allow controlled exchange of the photo-activatable substance between the organic cavity and a blood vessel, and
wherein the balloon is elastic and configured to surround the injection cannula.

13. An organic cavity injection method, comprising:
injecting, using an injection cannula, a photo-activatable substance inside an organic cavity, the photo-activatable substance having a non-activated state and an activated state wherein the photo-activatable substance is solidified by electromagnetic radiation in the activated state, wherein the photo-activatable substance is an inert, biocompatible liquid in the non-activated state;
simultaneous with injecting a photo-activatable substance inside an organic cavity, controllably removing, with a balloon placed in front of the organic cavity, a resident substance from the organic cavity and preventing flow of the photo-activatable substance that is in the non-activated state from the organic cavity, the balloon being configured for active, on/off control of the flow, the balloon being elastic and configured to surround the injection cannula, and the balloon is configured to have a direction of deformation that is controlled; and
providing electromagnetic radiation, through an optical waveguide inside the injection cannula, inside the organic cavity to the photo-activatable substance to photoactivate the photo-activatable substance and change the photo-activatable substance into the activated state inside the organic cavity;
wherein the photo-activatable substance comprises a photopolymerizable or photocurable material, and the balloon absorbs or reflects the electromagnetic radiation provided by the optical waveguide inside the organic cavity.

14. The method according to claim 13, wherein the step of providing electromagnetic radiation inside the organic cavity includes inserting the optical waveguide inside the organic cavity to directly place the optical waveguide in contact with the photo-activatable substance to achieve effective and fast photo-activation.

15. The method according to claim 14, further comprising substantially filling the organic cavity with a portion of the optical waveguide and enclosing the portion of the optical waveguide present in the organic cavity in the photo-activatable substance.

16. The method according to claim 14, wherein the optical waveguide includes a principal waveguide and a plurality of secondary waveguides to spatially distribute the electromagnetic radiation propagated by the principal waveguide throughout the photo-activatable substance and organic cavity.

17. The method according to claim 16, further comprising detaching the optical waveguide or the plurality of secondary waveguides from the optical waveguide to permanently leave the optical waveguide or plurality of secondary waveguides inside the organic cavity.

18. The method according to claim 17, wherein the optical waveguide is integrated into the injection cannula or is part of the injection cannula.

19. The method according to claim 13, further comprising providing a diffuser to diffuse the electromagnetic radiation provided by the optical waveguide throughout the photo-activatable substance and the organic cavity to achieve effective and fast photo-activation.

20. The method according to claim 19, further comprising injecting a plurality of scattering particles contained in an injection material into the organic cavity to diffuse the electromagnetic radiation provided by the optical waveguide throughout the photo-activatable substance and the organic cavity to achieve effective and fast photo-activation.

21. The method according to claim 13, further comprising incrementally inflating the balloon by predetermined volume amounts to control the removal of the resident substance from the organic cavity and prevent removal of the non-activated photo-activatable substance from the organic cavity such that a controlled exchange of the non-activated photo-activatable substance is facilitated from the organic cavity to a blood vessel.

22. The method according to claim 13 further comprising confining the electromagnetic radiation provided by the optical waveguide inside the organic cavity and the balloon is configured to prevent the photo-activation of the photo-activatable substance outside the organic cavity.

23. An organic cavity closure apparatus, comprising:
an injection cannula having a photo-activatable substance and configured for injecting the photo-activatable substance inside an organic cavity, the photo-activatable substance having a first state and a second state, the photoactivatable substance flowing through the injection cannula in the first state;

at least one element inserted with the injection cannula to control the flow of a resident substance from the organic cavity and simultaneously prevent flow of the photo-activatable substance from the organic cavity, the at least one element being configured for active, on/off control of the flow, at least part of the at least one element being elastic and configured to surround the injection cannula, and the at least one element being configured to have a direction of deformation that is controlled; and an optical waveguide inside the injection cannula and configured to emit electromagnetic radiation inside the organic cavity to convert the photo-activatable substance to the second state inside the organic cavity while the at least one element prevents flow of the photo-activatable substance from the organic cavity and configured for controlled exchange of the non-activated photo-activatable substance from the organic cavity to a blood vessel, wherein, in the second state, the photo-activatable substance is solidified by the electromagnetic radiation inside the organic cavity.

* * * * *